United States Patent
Dziubinski

(10) Patent No.: US 12,369,837 B2
(45) Date of Patent: Jul. 29, 2025

(54) ELECTROCARDIOGRAM SIGNAL SEGMENTATION

(71) Applicant: MEDICALgorithmics S.A., Warsaw (PL)

(72) Inventor: Marek Dziubinski, Warsaw (PL)

(73) Assignee: MEDICALgorithmics S.A., Warsaw (PL)

( * ) Notice: Subject to any disclaimer, the term of this patent is extended or adjusted under 35 U.S.C. 154(b) by 587 days.

(21) Appl. No.: 17/617,460

(22) PCT Filed: Apr. 22, 2020

(86) PCT No.: PCT/EP2020/061164
§ 371 (c)(1),
(2) Date: Dec. 8, 2021

(87) PCT Pub. No.: WO2020/221632
PCT Pub. Date: Nov. 5, 2020

(65) Prior Publication Data
US 2022/0218262 A1      Jul. 14, 2022

Related U.S. Application Data

(60) Provisional application No. 62/840,544, filed on Apr. 30, 2019.

(51) Int. Cl.
*A61B 5/352* (2021.01)
*A61B 5/00* (2006.01)
(Continued)

(52) U.S. Cl.
CPC ............ *A61B 5/352* (2021.01); *A61B 5/0006* (2013.01); *A61B 5/327* (2021.01); *A61B 5/353* (2021.01);
(Continued)

(58) Field of Classification Search
CPC ....... A61B 5/349; A61B 5/318; A61B 5/7264; A61B 5/0006; A61B 5/7282; A61B 5/366;
(Continued)

(56) References Cited

U.S. PATENT DOCUMENTS 9,986,951 B1 * 6/2018 Ferdosi ................. A61B 5/352
2015/0223759 A1 * 8/2015 Ong ....................... A61B 5/361
600/301
(Continued)

FOREIGN PATENT DOCUMENTS

EP        3644220 A1    4/2020

OTHER PUBLICATIONS

Response filed Jun. 1, 2022 to Communication pursuant to Rule 161(1)/Rule 162 EPC dated Dec. 7, 2021 for Application No. 20723297.6; 20 Pages.
(Continued)

*Primary Examiner* — Deborah L Malamud
(74) *Attorney, Agent, or Firm* — Daly, Crowley, Mofford & Durkee, LLP

(57) ABSTRACT

Techniques are disclosed for segmenting electrocardiogram (ECG) signals. In one example, a method to segment an electrocardiogram (ECG) signal may include detecting consecutive heartbeats in an ECG signal. The method also includes segmenting the ECG signal into multiple ECG segments surrounding the detected consecutive heartbeats and generating an ECG data set by joining consecutive ECG segments. The generated the ECG data set represents the detected heartbeats. In some such examples, each ECG segment is of a duration to include a QRS complex, a P wave, and a T wave.

19 Claims, 8 Drawing Sheets

(51) Int. Cl.
    *A61B 5/327*    (2021.01)
    *A61B 5/353*    (2021.01)
    *A61B 5/355*    (2021.01)
    *A61B 5/366*    (2021.01)
(52) U.S. Cl.
    CPC .............. *A61B 5/355* (2021.01); *A61B 5/366* (2021.01); *A61B 2560/02* (2013.01)
(58) Field of Classification Search
    CPC ....... A61B 5/7246; A61B 5/364; A61B 5/346; A61B 5/02; A61B 5/308; A61B 5/7235; A61B 5/28; A61B 5/0004; A61B 5/05; A61B 5/00; A61N 1/00
    See application file for complete search history.

(56)    References Cited

U.S. PATENT DOCUMENTS

| | | |
|---|---|---|
| 2016/0198969 A1 | 7/2016 | Cheng et al. |
| 2017/0360377 A1 | 12/2017 | Rossi et al. |
| 2018/0249961 A1 | 9/2018 | Ferdosi et al. |
| 2020/0155024 A1 | 5/2020 | Wang et al. |

OTHER PUBLICATIONS

International Search Report and Written Opinion dated Jul. 29, 2020 for PCT Application No. PCT/EP2020/061164; 13 Pages.

\* cited by examiner

ELECTROCARDIOGRAM SIGNAL SEGMENTATION

CROSS REFERENCE TO RELATED APPLICATION

This application is a U.S. national stage filing under 35 U.S.C § 371 of PCT application number PCT/EP2020/061164 filed on Apr. 22, 2020, and entitled "ELECTROCARDIOGRAM SIGNAL SEGMENTATION" which is based on and claims priority to U.S. Patent Application No. 62/840,544, filed on Apr. 30, 2019 which applications are each hereby incorporated herein by reference in their entireties.

BACKGROUND

An electrocardiogram (ECG) is a medical test that records the electrical activity generated by the heart using electrodes placed at well-established locations on the skin. These electrodes record cardiac electrical signals that are a result of cardiac muscle depolarization followed by repolarization during each cardiac cycle (heartbeat). The recorded cardiac electrical activity, represented by a graph of voltage over time, can be interpreted to detect numerous cardiac abnormalities. For example, a doctor may recommend an ECG for a person who may be at risk of heart disease because there is a family history of heart disease, or because they smoke, are overweight, have diabetes, high cholesterol, or high blood pressure. A doctor may also recommend an ECG for person who is displaying certain symptoms such as chest pain, breathlessness, dizziness, fainting, or fast or irregular heartbeats. In any case, ECG allows for detection of cardiac problems in their early stages and prevention of further costly complications that may arise from such cardiac problems.

An ECG provides a snapshot of the electrical activity of the heart recorded over a short duration of time, such as a few minutes. To a trained observer, an ECG can convey a large amount of information regarding the structure and function of the heart present at the time of recording (e.g., present during the 10 seconds of the ECG recording). As such, an ECG is effective for detection of cardiac conditions that are captured during the short duration of the ECG recording but is ineffective for diagnosis of cardiac conditions that may not be captured during the relatively short ECG recording. To this end, diagnostic efficacy of many cardiac conditions can be improved through long-term, extended ECG monitoring.

SUMMARY

This Summary is provided to introduce a selection of concepts in simplified form that are further described below in the Detailed Description. This Summary is not intended to identify key or essential features or combinations of the claimed subject matter, nor is it intended to be used to limit the scope of the claimed subject matter.

According to one illustrative example embodiment, a method to segment an electrocardiogram (ECG) signal may include detecting consecutive heartbeats in an ECG signal, segmenting the ECG signal into multiple ECG segments surrounding the detected consecutive heartbeats, and generating an ECG data set by joining consecutive ECG segments, wherein the ECG data set represents the detected heartbeats. In embodiments, the segmented data described herein and dataset preparation may be useful for training of machine learning systems. The segmented data described herein and dataset preparation may be useful for use with machine learning methods and systems. In embodiments, the systems, devices and segmentation techniques described herein may be used in data preparation methods for machine learning. In an embodiment, a remote cardiac monitoring system includes a portable patient monitor and a cardiac monitoring station, which includes a trained ECG interpretation module for predicting the existence of cardiac conditions in ECG monitoring data. Such a portable patent monitor may be operable to acquire and record ECG signals from a patient and transmit the ECG data to the cardiac monitoring station. The cardiac monitoring station receives the ECG data and, utilizing the trained ECG interpretation module, makes a prediction (e.g., inference) as to the existence (or non-existence) of a cardiac condition as manifested by the input ECG data.

According to another illustrative example embodiment, a system to segment an electrocardiogram (ECG) signal includes one or more non-transitory machine-readable mediums configured to store instructions, and one or more processors configured to execute the instructions stored on the one or more non-transitory machine-readable mediums. Execution of the instructions causes the one or more processors to detect N consecutive heartbeats in an ECG signal, segment the ECG signal into multiple ECG segments surrounding the detected N consecutive heartbeats, and generate an ECG data set by joining consecutive ECG segments, wherein the ECG data set represents the detected N heartbeats.

According to still another illustrative example embodiment, a computer program product includes one or more non-transitory machine-readable mediums encoding instructions that when executed by one or more processors cause a process to be carried out for segmenting an electrocardiogram (ECG) signal. The process includes detecting consecutive heartbeats in an ECG signal, segmenting the ECG signal into multiple ECG segments surrounding the detected consecutive heartbeats, wherein each ECG segment of the multiple ECG segments is of a duration to include a QRS complex, a P wave, and a T wave, and generating an ECG data set by joining consecutive ECG segments.

BRIEF DESCRIPTION OF THE DRAWINGS

The foregoing and other objects, features and advantages will be apparent from the following more particular description of the embodiments, as illustrated in the accompanying drawings in which like reference characters refer to the same parts throughout the different views. The drawings are not necessarily to scale, emphasis instead being placed upon illustrating the principles of the embodiments.

DETAILED DESCRIPTION

Figure 1:
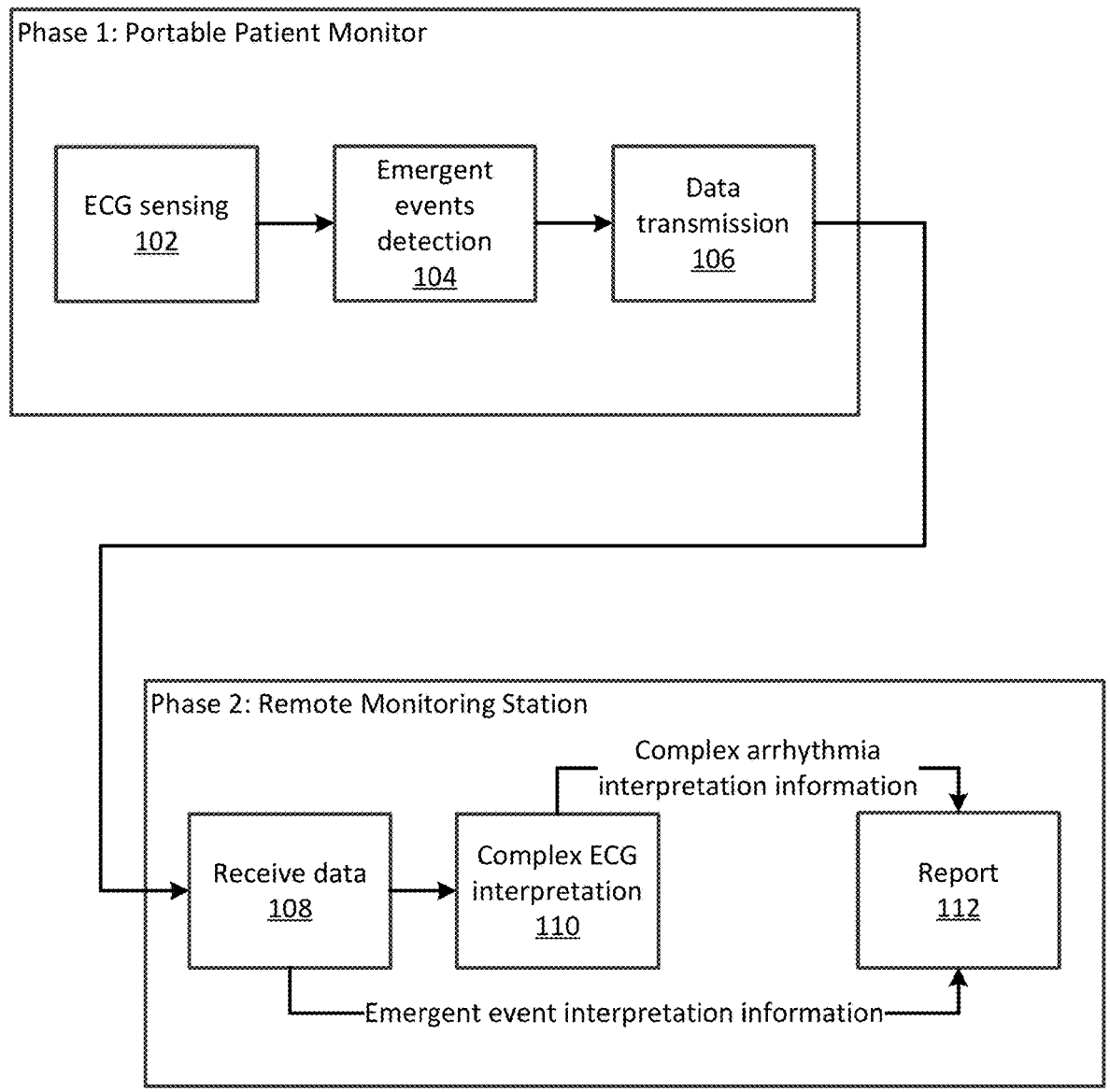
FIG. 1 is a diagram illustrating an example process flow for a two-phase remote ECG monitoring, in accordance with an embodiment of the present disclosure.

In the following description of the various embodiments, reference is made to the accompanying drawings identified above and which form a part hereof, and in which is shown by way of illustration various embodiments in which aspects of the concepts described herein may be practiced. It is to be understood that other embodiments may be utilized, and structural and functional modifications may be made without departing from the scope of the concepts described herein. It should thus be understood that various aspects of the concepts described herein may be implemented in embodiments other than those specifically described herein. It should also be appreciated that the concepts described herein are capable of being practiced or being carried out in ways which are different than those specifically described herein.

As noted above, numerous efficiencies and benefits can be derived from long-term, extend ECG monitoring. For example, remote ECG monitoring using devices such as a Holter monitor, a wireless ambulatory ECG, or an implantable loop recorder, to provide a few examples, can be used for extending the monitoring duration beyond one day or a few days. Such extended monitoring may allow for detection of cardiac conditions such as intermittent arrhythmia (atrial fibrillation) or other sporadic conditions. However, long-term, extended ECG monitoring generates a large amount of ECG signal data that need to be processed and reviewed by trained medical professionals to perform a proper diagnosis of the patient (e.g., to determine the presence of a cardiac condition). ECG signal segmentation is one very important stage in the proper processing of ECG signals.

Thus, and in accordance with an embodiment of the present disclosure, techniques are disclosed for segmenting an ECG. According to an embodiment, consecutive heartbeats are detected in an ECG signal and marked. In one example implementation, each detected heartbeat can be marked with a black dot or other suitable indicator at a location above a QRS complex to indicate the location of a heartbeat associated with the QRS complex. The ECG signal is then segmented or otherwise broken into fixed-size ECG segments surrounding the detected consecutive heartbeats. In one such embodiment, an ECG segment is of sufficient duration (length) to include a QRS complex, a P wave to the right of the QRS complex, and a T wave to the left of the QRS complex. An ECG data set representing the detected heartbeats is then generated by joining the fixed-size consecutive ECG segments to reconstruct the ECG signal.

In some embodiments, a non-overlap between adjacent ECG segments are identified, and an artificial heartbeat marker is included in the ECG data set, wherein the artificial heartbeat marker indicates an ECG fragment between the non-overlapping ECG segments.

In some such embodiments, additional information, such as heart rate information and/or other features regarding a heartbeat, can be included in the ECG data set. Such additional information can be specified using feature vectors, where each vector includes features specific for a given heartbeat. By way of an example, and in one example implementation, each feature vector may contain information describing P-wave information, T-wave information including onset location, offset location, duration, shape/morphology, amplitude, other waves information including Q, R and S characteristics, morphologies, durations, amplitudes, noise level information surrounding the given heartbeat and acceleration information (e.g., the acceleration information can be measured and provided by an accelerometer included in the patient portable monitor), and other information such as beat information collected from non-ECG sensors, including PPG signal, blood pressure signal, and blood oxygen saturation information, to provide some examples. These and other advantages and alternative embodiments will be apparent in light of this disclosure.

It is to be understood that the phraseology and terminology used herein are for the purpose of description and should not be regarded as limiting. Rather, the phrases and terms used herein are to be given their broadest interpretation and meaning. The use of "including" and "comprising" and variations thereof is meant to encompass the items listed thereafter and equivalents thereof as well as additional items and equivalents thereof. The use of the terms "connected," "coupled," and similar terms, is meant to include both direct and indirect, connecting, and coupling.

Turning now to the figures, FIG. 1 is a diagram illustrating an example process flow for a two-phase remote ECG monitoring, in accordance with an embodiment of the present disclosure. The two-phase remote ECG monitoring includes a phase 1 that is performed or otherwise implemented using a portable patient monitor and a phase 2 that is performed or otherwise implemented using a remote monitoring system. As shown, phase 1 includes an ECG sensing subphase 102, an emergent events detection subphase 104, and a data transmission subphase 106, and phase 2 includes a receive data subphase 108, a complex ECG interpretation subphase 110, and a report subphase 112. As will be appreciated, these phases and subphases are used for purposes facilitating discussion and should not be construed as structural or otherwise rigid limitations. For instance, the EGC sensing subphase and the emergent events detection subphase may be combined into a single subphase occurring prior to the data transmission subphase. As another example, the complex ECG interpretation subphase can be split or separated into multiple subphases, for example, based on the number of non-emergent events. In short, any number of phases and subphases can be used to provide the various functionality provided herein. Numerous embodiments will be apparent.

In an example use case of the remote monitoring, a patient may be carrying the portable patient monitor, such as a Holter monitor, a wireless ambulatory ECG, or an implantable loop recorder, for the monitoring of the patient's heart. ECG sensing subphase 102 includes acquiring an ECG signal from the patient's body. ECG sensing subphase 102 can also include digitizing the acquired ECG signal. Emergent events detection subphase 104 includes analyzing or otherwise processing the ECG signal to detect emergent events that are manifested in the ECG signal. As these are emergent events, the emergent events detection processing can be performed by the portable patient monitor with minimal delay. In some embodiments, the portable patient monitor can provide a notification, such as a visual, auditory, and/or haptic notification, to provide a few examples, informing of the detection of an emergent event. Data transmission subphase 106 includes transmitting or otherwise providing the ECG signal data to the remote monitoring system. In one embodiment, the ECG signal data can be transmitted once an emergent event is detected. This allows for further analysis or processing of the ECG signal by the remote monitoring system. In some such embodiments, notification of the detected emergent event as well as information regarding the detected emergent event (e.g., emergent event interpretation information) can also be transmitted or otherwise provided to the remote monitoring system. In cases where an emergent event is not detected, the portable patient monitor can buffer (e.g., store) the ECG signal data, and transmit or otherwise provide the buffered ECG signal data periodically, such as every 30 secs., 60 secs, 2 mins., 5 mins, 10 mins, or other suitable period of time.

Receive data subphase 108 includes receiving the ECG signal data transmitted or otherwise provided by the portable patient monitor. Receive data 108 may also include providing any emergent event interpretation information that is provided with the ECG signal data for reporting to a physician, health care professional, and/or other trained monitoring personnel, for instance. For example, providing notification of an emergent event detected by the portable patient monitor can allow the physician or monitoring personnel to immediately (or without undue delay) access the ECG signal data and appropriately tend to the patient. Complex ECG interpretation subphase 110 includes performing non-emergent ECG signal interpretation, such as analyzing the ECG signal for complex arrhythmia interpretation information, for example. In some embodiments, the non-emergent ECG signal interpretation can utilize broad ECG signal context and/or large ECG signal buffers (e.g., a relatively large length or duration of the ECG signal) to improve and/or optimize the accuracy and depth of the ECG signal interpretation. Report subphase 112 includes generating ECG signal diagnostic reports. The reports may include diagnostic reports of the emergent events detected by the portable patient monitor and/or diagnostic reports of the non-emergent ECG signal interpretation performed by the remote monitoring station.

Remote ECG monitoring using a portable patient monitor and a remote monitoring station is further described below with respect to FIGS. 7 and 8.

Figure 2:
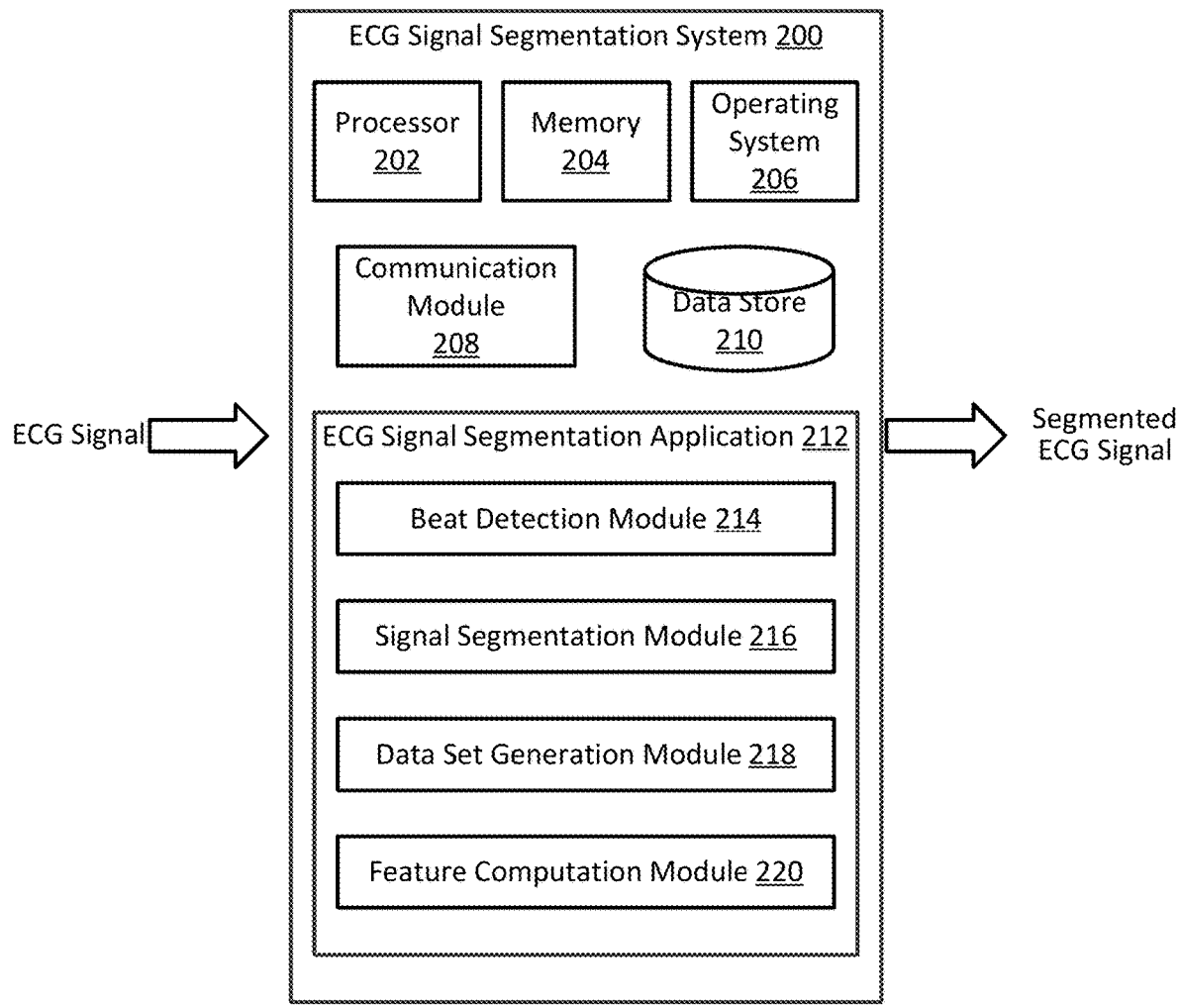
FIG. 2 is a block diagram illustrating selected components of an example ECG signal segmentation system that is programmed with or otherwise includes an ECG signal segmentation application, in accordance with an embodiment of the present disclosure.

FIG. 2 is a block diagram illustrating selected components of an example ECG signal segmentation system 200 that is programmed with or otherwise includes an ECG signal segmentation application, in accordance with an embodiment of the present disclosure. In some embodiments, ECG signal segmentation system 200 can be implemented using a computer system, such as a workstation, desktop computer, server, laptop, handheld computer, tablet computer (e.g., the iPad tablet computer), mobile computer or communication device (e.g., the iPhone mobile communication device, the Android mobile communication device, and the like), or other form of computing or telecommunication device that is capable of communication and that has sufficient processing power and memory capacity to perform the operations described in this disclosure. In some embodiments, a distributed computational system is provided comprising multiple of such computing systems. As shown in FIG. 2, ECG signal segmentation system 200 includes a processor 202, a memory 204, an operating system 206, a communication module 208, a data store 210, and an ECG signal segmentation application 212. In various embodiments, additional components (not illustrated, such as a display, input/output interface, user interface, etc.) or a subset of the illustrated components can be employed without deviating from the scope of the present disclosure. For instance, in various embodiments, ECG signal segmentation application 212 may not include one or more of the components illustrated in FIG. 2, but ECG signal segmentation application 212 may connect or otherwise couple to the one or more components via a communication interface.

Processor 202 may be designed to control the operations of the various other components of ECG signal segmentation system 200. Processor 202 may include any processing unit suitable for use in ECG signal segmentation system 200, such as a single core or multi-core processor. In general, processor 202 may include any suitable special-purpose or general-purpose computer, computing entity, or computing or processing device including various computer hardware, or firmware, and may be configured to execute instructions, such as program instructions, stored on any applicable computer-readable storage media. For example, processor 202 may include a microprocessor, a central processing unit (CPU), a microcontroller, a digital signal processor (DSP), an application-specific integrated circuit (ASIC), a Field-Programmable Gate Array (FPGA), Complex Instruction Set Computer (CISC), Reduced Instruction Set Computer (RISC), multi core, or any other digital or analog circuitry configured to interpret and/or to execute program instructions and/or to process data, whether loaded from memory or implemented directly in hardware. Although illustrated as a single processor in FIG. 2, processor 202 may include any number of processors and/or processor cores configured to, individually or collectively, perform or direct performance of any number of operations described in the present disclosure.

Memory 204 may include computer-readable storage media configured for carrying or having computer-executable instructions or data structures stored thereon. Such computer-readable storage media may include any available media that may be accessed by a general-purpose or special-purpose computer, such as processor 202. By way of example, and not limitation, such computer-readable storage media may include non-transitory computer-readable storage media including Random Access Memory (RAM), Dynamic Random Access Memory (DRAM), Synchronized Dynamic Random Access Memory (SDRAM), Static Random Access Memory (SRAM), a redundant array of independent disks (RAID), non-volatile memory (NVM), or any other suitable storage medium which may be used to carry or store particular program code in the form of computer-executable instructions or data structures and which may be accessed by a general-purpose or special-purpose computer. Combinations of the above may also be included within the scope of computer-readable storage media.

Operating system 206 may comprise any suitable operating system, such as UNIX®, LINUX®, MICROSOFT® WINDOWS® (Microsoft Crop., Redmond, WA), GOOGLE® ANDROID™ (Google Inc., Mountain View, CA), APPLE® iOS (Apple Inc., Cupertino, CA), or APPLE® OS X® (Apple Inc., Cupertino, CA). As will be appreciated in light of this disclosure, the techniques provided herein can be implemented without regard to the particular operating system provided in conjunction with ECG signal segmentation system 200, and therefore may also be implemented using any suitable existing or subsequently developed platform.

Communication module 208 can be any appropriate network chip or chipset which allows for wired or wireless communication via a network and/or communication link (such as a network 706 further described below) to one or more of the other components described herein. Communication module 208 can also be configured to provide intra-device communications via a bus or an interconnect.

Data store 210 may include any type of computer-readable storage media configured for short-term or long-term storage of data. By way of example, and not limitation, such computer-readable storage media may include a hard drive, solid-state drive, Read-Only Memory (ROM), Electrically Erasable Programmable Read-Only Memory (EEPROM), Compact Disc Read-Only Memory (CD-ROM) or other optical disk storage, magnetic disk storage or other magnetic storage devices, flash memory devices (e.g., solid state memory devices), non-volatile memory (NVM), or any other storage medium, including those provided above in conjunction with memory 204, which may be used to carry or store particular program code in the form of computer-readable and computer-executable instructions, software or data structures for implementing the various embodiments as disclosed herein and which may be accessed by a general-purpose or special-purpose computer. Combinations of the above may also be included within the scope of computer-readable storage media. Data store 210 may be provided on ECG signal segmentation system 200 or provided separately or remotely from ECG signal segmentation system 200.

As further shown in FIG. 2, ECG signal segmentation application 212 includes a beat detection module 214, a signal segmentation module 216, a data set generation module 218, and a feature computation module 220. ECG signal segmentation application 212 is configured to facilitate the segmenting of an ECG, such as an ECG signal input or otherwise provided to ECG segmentation system 200. The ECG signal may represent a plot of the bio-potential generated by the activity of a heart.

Figure 3:
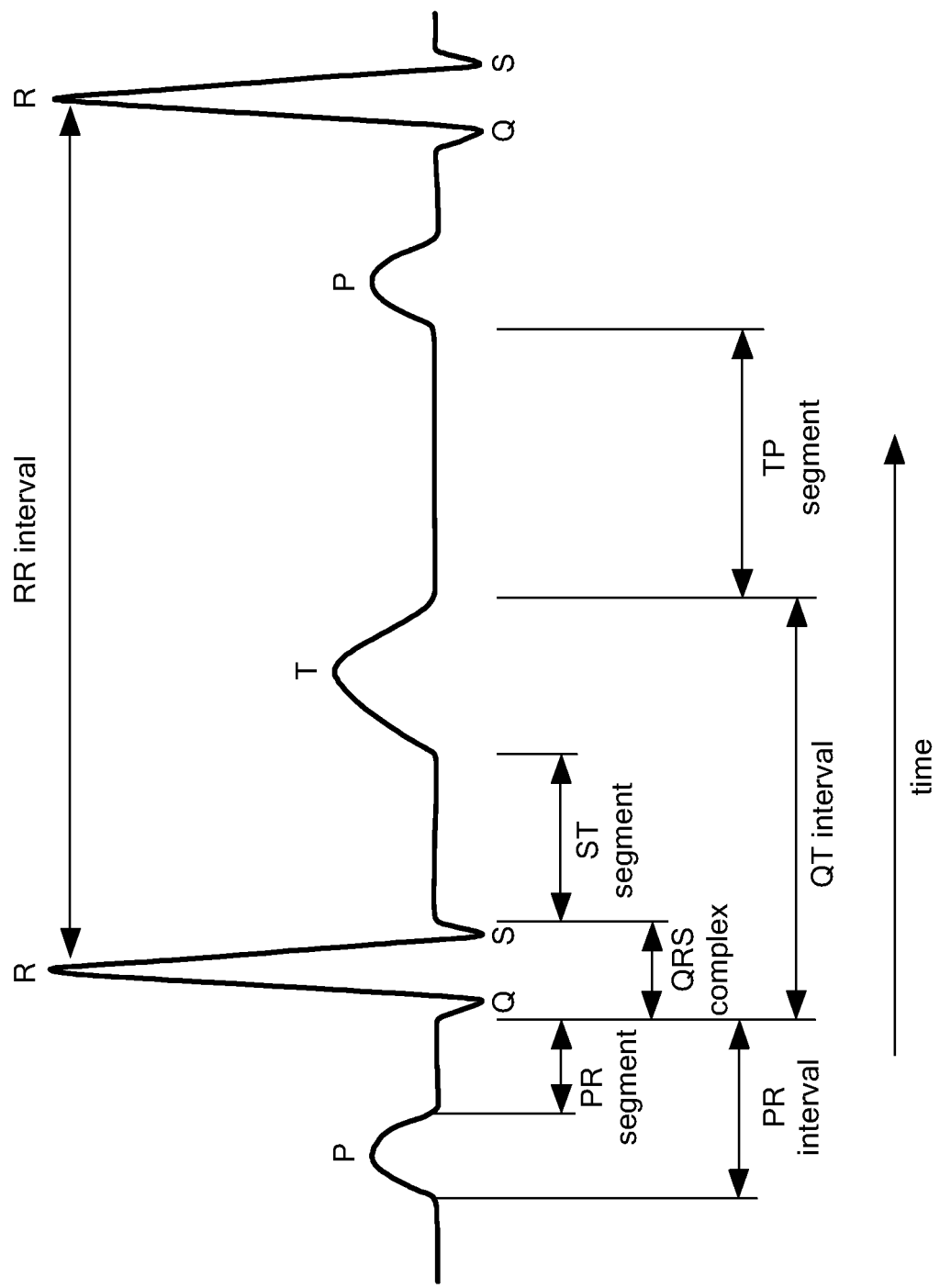
FIG. 3 is a diagram illustrating an example waveform output from an electrocardiogram (ECG) for a single cardiac cycle.

FIG. 3 is a diagram illustrating an example waveform output from an electrocardiogram (ECG) for a single cardiac cycle. More specifically, FIG. 3 shows single cardiac cycle (single heart beat), with a description of ECG peaks, waves, and intervals, which are the basis of ECG analysis and classification. As shown, a typical ECG waveform or tracing of a normal heartbeat (or cardiac cycle) includes a P wave, a QRS complex (also known as a QRS interval), and a T wave. A small U wave (not shown) is normally visible in about 50% to 75% of ECGs. The baseline voltage of the electrocardiogram is known as an isoelectric line. Typically, the isoelectric line is measured as the portion of the tracing following the T wave and preceding the next P wave.

The P Wave is seen during normal atrial depolarization, a mean electrical vector is directed from the SA node towards the AV node, and spreads from the right atrium to the left atrium. The relationship between the P waves and the QRS complexes helps with distinguishing various cardiac arrhythmias. For example, the shape and duration of the P waves may indicate atrial enlargement.

The PR segment is to the left of the QRS complex. The PR segment is the flat line between the end of the P wave and the start of the QRS complex. The PR segment reflects the time delay between the atrial and ventricular activation. The PR segment also serves as the baseline of the ECG curve. A PR segment depression may indicate atrial injury or pericarditis.

The PR interval is measured from the beginning of the P wave to the beginning of the QRS complex. The PR interval is usually about 120 to 200 ms in duration. On an ECG tracing, this can correspond to 3 to 5 small boxes, depending on the grid size. A prolonged PR interval may indicate a first degree heart block; a short PR interval may indicate a pre-excitation syndrome via an accessory pathway that leads to early activation of the ventricles, such as seen in Wolff-Parkinson-White syndrome; a variable PR interval may indicate other types of heart block; a PR interval depression may indicate atrial injury or pericarditis; and variable morphologies of P waves in a single ECG lead is suggestive of an ectopic pacemaker rhythm, such as wandering pacemaker or multifocal atrial tachycardia.

The QRS complex is a structure on the ECG that corresponds to the depolarization of the ventricles. Because the ventricles contain more muscle mass than the atria, the QRS complex is typically larger than the P wave. In addition, because the His-Purkinje system coordinates the depolarization of the ventricles, the QRS complex tends to look or appear "spiked" rather than rounded due to the increase in conduction velocity. A normal QRS complex is about 0.06 to 0.10 sec (about 60 to 100 ms) in duration. The duration, amplitude, and morphology of the QRS complex is useful in diagnosing cardiac arrhythmias, conduction abnormalities, ventricular hypertrophy, myocardial infarction, electrolyte derangements, and other disease states. The Q wave can be normal (physiological) or pathological.

The ST segment is to the right of the QRS complex. The ST segment connects the QRS complex and the T wave and has a duration of about 0.005 to 0.150 sec (about 5 to 150 ms). The ST segment starts at a J point (junction between the QRS complex and the ST segment and ends at the beginning of the T wave. However, since it is usually difficult to determine exactly where the ST segment ends and the adjoining T wave begins, the relationship between the ST segment and the T wave is typically examined together. The typical ST segment duration is usually about 0.08 sec (about 80 ms). It should be essentially level with the PR segment and the TP segment. The shape of a normal ST segment has a slight upward concavity. Flat, downsloping, or depressed ST segments may indicate coronary ischemia, while elevated ST segment may indicate myocardial infarction.

The T wave represents the repolarization (or recovery) of the ventricles. The interval from the beginning of the QRS complex to the apex of the T wave is referred to as the absolute refractory period. The last half of the T wave is referred to as the relative refractory period (or vulnerable period). Inverted (or negative) T waves can be a sign of coronary ischemia, Wellens' syndrome, left ventricular hypertrophy, or CNS disorder. Tall or "tented" symmetrical T waves may indicate hyperkalemia. Flat T waves may indicate coronary ischemia or hypokalemia.

The QT interval is measured from the beginning of the QRS complex to the end of the T wave. A normal QT interval is usually about 0.40 seconds. The QT interval as well as the corrected QT interval are useful in the diagnosis of long QT syndrome and short QT syndrome and also are useful in ventricular tachyarrhythmia prediction.

The TP segment is the isoelectric interval on the ECG. It is the region between the end of the T wave and the next P wave. The TP segment represents the time when the heart muscle cells are electrically silent. The duration or length of the TP segment shortens when the heart rate increases and vice versa.

The U wave is typically small, and not always seen, and by definition, follows the T wave. U waves are thought to represent repolarization of the papillary muscles or Purkinje fibers. Prominent U waves are most often seen in hypokalemia, but may be present in hypercalcemia, thyrotoxicosis, or exposure to digitalis, epinephrine, and Class 1A and Class 3 antiarrhythmics, as well as in congenital long QT syndrome and in the setting of intracranial hemorrhage. An inverted U wave may represent myocardial ischemia or left ventricular volume overload.

Referring again to FIG. 2, beat detection module 214 is configured to detect consecutive heartbeats in the ECG signal. In one example embodiment, beat detection module 214 can detect N consecutive heartbeats. Beat detection module 214 is also configured to mark each detected heartbeat to indicate the location of the heartbeat. In one example implementation, each detected heartbeat can be marked with a black dot or other suitable indicator at a location above a QRS complex to indicate the location of a heartbeat associated with the QRS complex.

Signal segmentation module 216 is configured to segment or otherwise break the ECG signal into fixed-size ECG segments surrounding the detected consecutive heartbeats. The duration or length of an ECG segment may be related to the averaged heart rate. In one such embodiment, an ECG segment is of sufficient duration (length) to include a QRS complex, a P wave to the right of the QRS complex, and a T wave to the left of the QRS complex.

Figure 4:
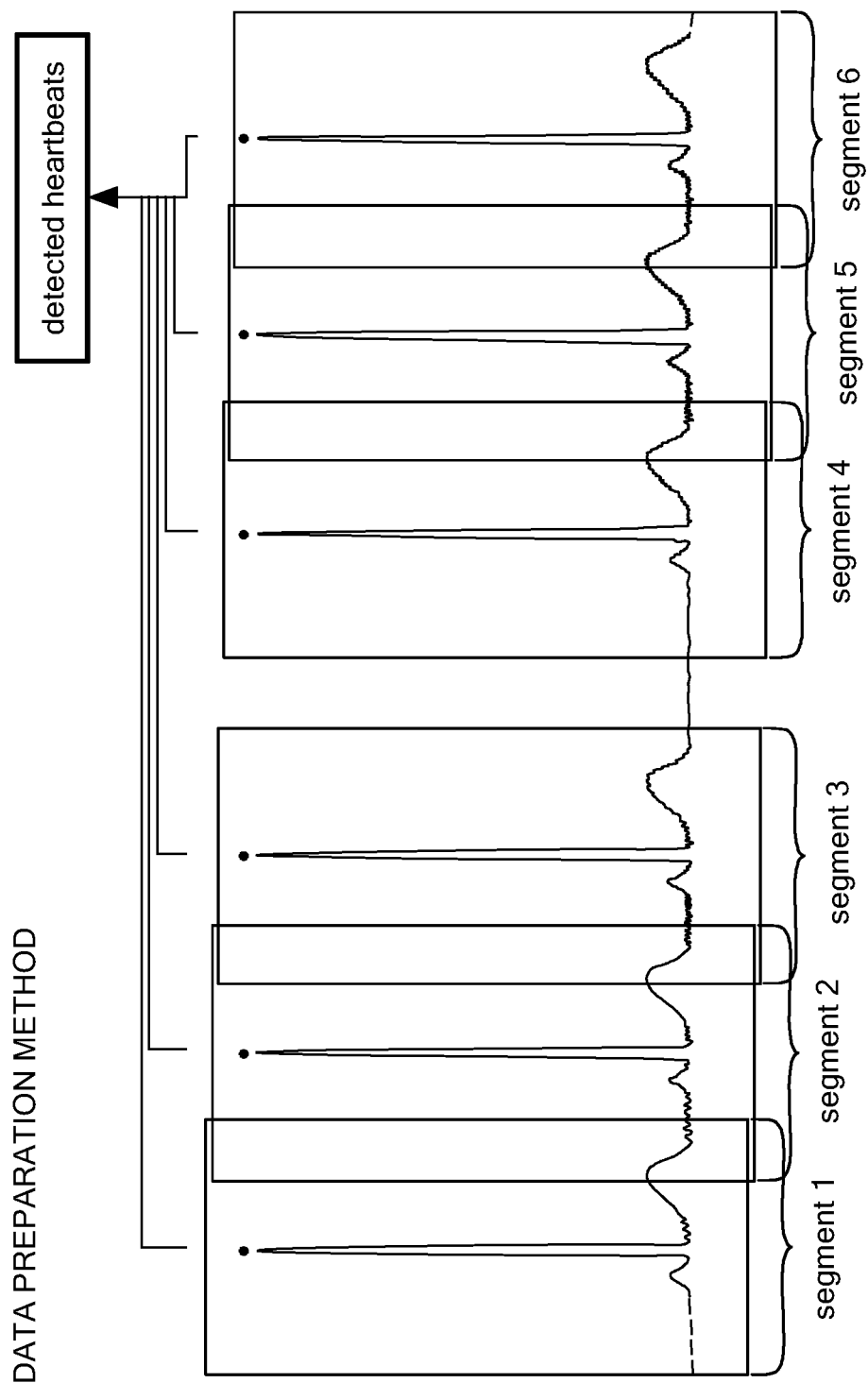
FIG. 4 is a diagram illustrating an example ECG signal segmented into fixed-size ECG segments, in accordance with an embodiment of the present disclosure.

FIG. 4 illustrates ECG signal segmentation method, where the consecutive heartbeats are detected and marked or otherwise identified. In FIG. 4, the heartbeats are marked with black dots located above the QRS complexes. In practical systems, after detection, the heartbeats are marked or otherwise identified electronically. The figure shows fixed size ECG segments surrounding the marked heartbeats (highlighted by gray rectangles in FIG. 4). It can be seen that all (except one) of the segments are overlapping, assuring that all (except one) of the ECG signal fragments are contained in the data. Also, it is shown in FIG. 4 that segments 3 and 4 are not overlapping, which results in an ECG fragment that is not contained in the data. The resolution to this problem has been shown in FIG. 5. It should be noted that the ECG signal shown in FIG. 4 may be a portion of the ECG signal that was input to and is being processed by ECG signal segmentation system 200 (e.g., being segmented by signal segmentation module 216). As shown, the ECG signal is segmented into six fixed-size ECG segments (e.g., segment 1, segment 2, segment 3, segment 4, segment 5, and segment 6). As shown, each ECG segment includes a single heartbeat. However, this may not be the case in all instances. That is, an ECG segment may include multiple heartbeats. For example, in the case of a patient having an accelerated heart rate, an ECG segment or multiple ECG segments can include multiple heartbeats. As can be seen in FIG. 4, each detected heartbeat in an ECG segment is appropriately marked (e.g., as indicated by the black dot appearing over each QRS complex). In embodiments, ECG segments of differing sizes may be used.

Referring again to FIG. 2, data set generation module 218 is configured to join the fixed-size consecutive ECG segments to generate an ECG data set. The ECG data set is a representation of the detected heartbeats in the ECG signal. As will be appreciated in light of this disclosure, any number of suitable techniques can be used to join the consecutive ECG segments.

Data set generation module 218 is also configured to identify any non-overlap between adjacent ECG segments. For each identified non-overlap between adjacent ECG segments, data segmentation module 218 includes an artificial heartbeat marker. The artificial heartbeat marker can be included in the ECG data set. The purpose of the artificial heartbeat marker is to indicate an ECG fragment between the non-overlapping ECG segments.

Figure 5:
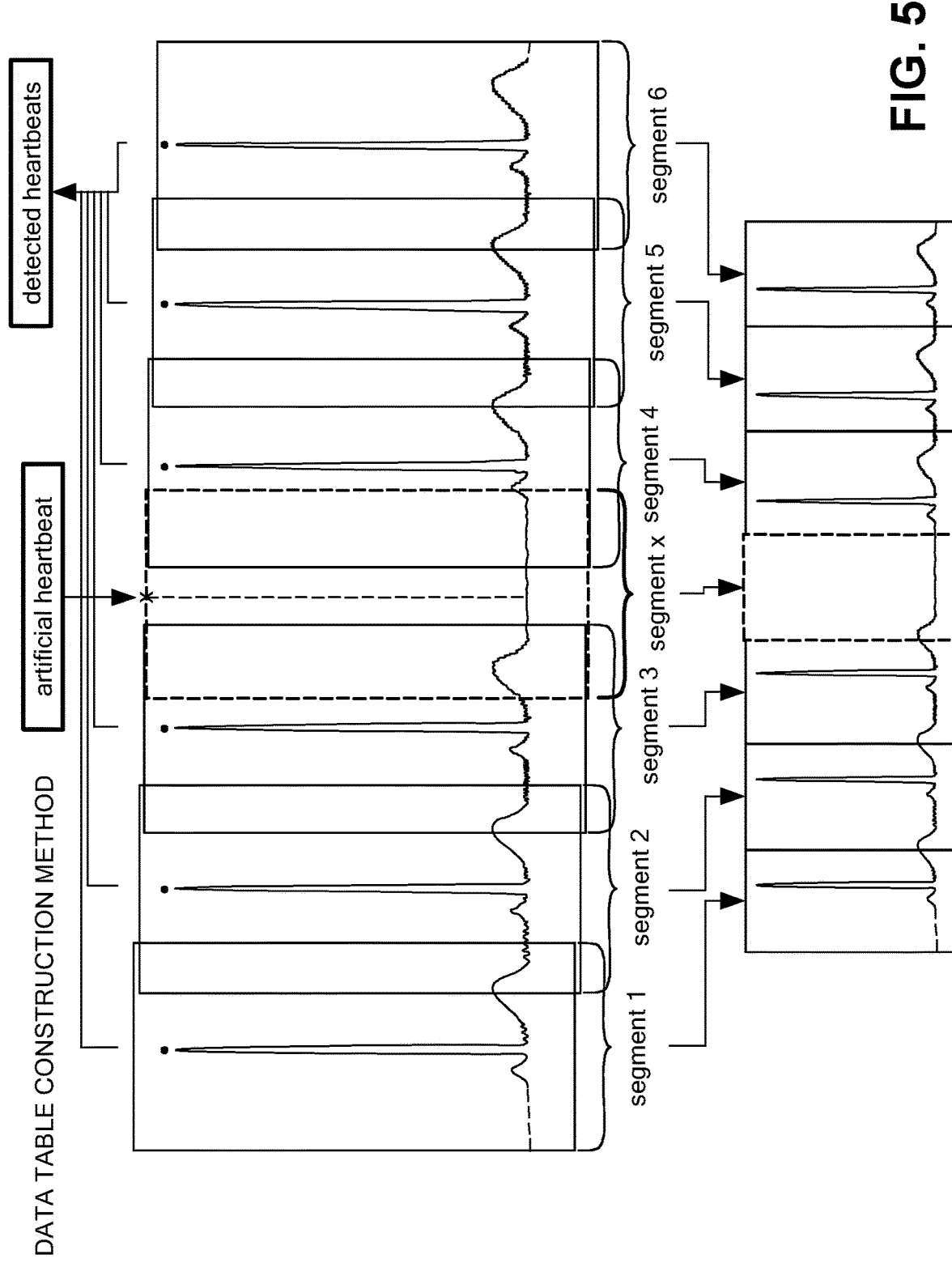
FIG. 5 is a diagram illustrating the ECG segments of FIG. 4 including an artificial heartbeat, in accordance with an embodiment of the present disclosure.

FIG. 5 shows the ECG signal segments illustrated in FIG. 4 including an artificial heartbeat. As can be seen, there is one non-overlap between adjacent ECG segments. Specifically, segment 3 and segment 4 do not overlap when the six ECG segments are joined. That is, segments 1 and 2 overlap, segments 2 and 3 overlap, segments 4 and 5 overlap, and segments 5 and 6 overlap. However, segments 3 and 4 do not overlap.

As can be further seen in FIG. 5, an artificial heartbeat marker (e.g., as indicated by an "x") is included between segments 3 and 4. The artificial heartbeat indicates a missing ECG fragment (e.g., segment x) in the ECG data set. Under some conditions, it may be necessary to include more than one artificial heartbeat marker in a missing ECG segment. FIG. 5. thus illustrates the construction of a machine learning data table and an introduction of an artificial beat (x) to include the not included ECG fragment between segment 3 and 4.

Referring again to FIG. 2, feature computation module 220 is configured to identify or otherwise determine (e.g., compute) properties or characteristics of the heartbeats. Examples of such properties or characteristics include heart rate information, information describing P-wave information, T-wave information including onset location, offset location, duration, shape/morphology, amplitude, other waves information including Q, R and S characteristics, morphologies, durations, amplitudes, noise level information surrounding the given heartbeat and acceleration information (e.g., measured and provided by an accelerometer included in the patient portable monitor), and other information such as beat information (e.g., collected from non-ECG sensors), including PPG signal, blood pressure signal, and blood oxygen saturation information, to provide some examples. In one example implementation, the identified properties or characteristics of the heartbeats can be included in one or more feature vectors. The feature vectors can be included in the ECG data set.

Figure 6:
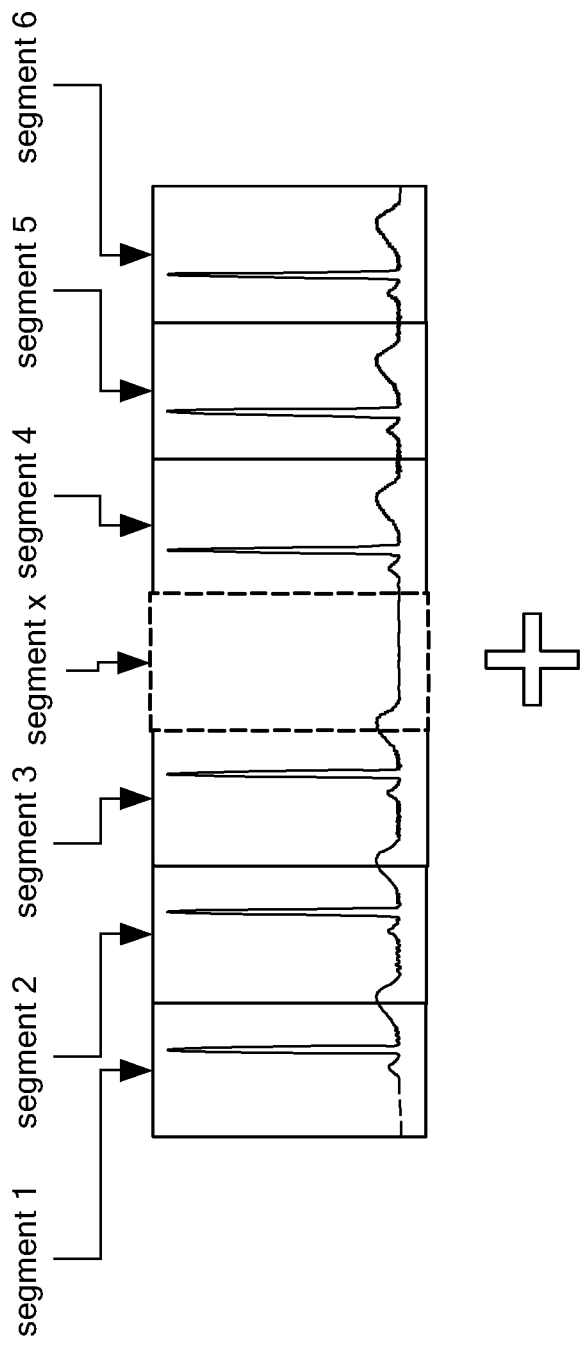
FIG. 6 is a diagram illustrating the ECG segments of FIG. 5 and associated features, in accordance with an embodiment of the present disclosure.

FIG. 6 shows the ECG signal segments illustrated in FIG. 5 and associated feature vectors. As can be seen, each heartbeat is associated with two feature vectors ("HR1, HR2, HR3, HRX, HR4, HR5, HR6" and ("FV1, FV2, FV3, FVX, FV4, FV5, FV6"). The feature vectors include information (properties, characteristics, etc.) specific for a given heartbeat. For example, the feature vector HRx may include heart rate information for each heartbeat. Likewise, the feature vector FVx may include other properties or characteristics for each heartbeat. Although FIG. 6 shows the use of two feature vectors, a different number of feature vectors (such as one, three, four, or more) can be used as will be appreciated in light of this disclosure, and this disclosure should not be construed as limited in this regard.

In embodiments, segment features may be calculated or otherwise determined in the same way (i.e. individually per each segment). In embodiments, the segment features may be calculated or otherwise determined in the same way for each segment. For example, if the features represent P, QRS and T morphological, they should be set to a predetermined or default value (e.g. a value of 0 or some other predetermined value). If the features are not related to the QRS complex but are objective measures of the signal, (e.g. noise level, standard deviation, mean value, etc.) they can be calculated for a missing segment (e.g. segment X).

In various embodiments, additional components or a subset of the illustrated components can be employed without deviating from the scope of the present disclosure. For instance, other embodiments may integrate the various functionalities of ECG signal segmentation application 212, including beat detection module 214, signal segmentation module 216, data set generation module 218, and feature computation module 220 into fewer modules (e.g., one or two) or more modules (e.g., four, five or six, or more). In addition, further note that the various components of ECG signal segmentation application 212 may all be in a stand-alone computing system according to some embodiments, while in others, may be distributed across multiple machines. For example, each of beat detection module 214, signal segmentation module 216, data set generation module 218, and feature computation module 220 can be located in a cloud-based server arrangement, and accessible to a client-based user interface via a communications network. In some cases, one or more of beat detection module 214, signal segmentation module 216, data set generation module 218, and feature computation module 220 may be downloaded from a cloud-based service into the browser (or other application) of a client computer for local execution. In a more general sense, the degree of integration and distribution of the functional component(s) provided herein can vary greatly from one embodiment to the next, as will be appreciated in light of this disclosure.

In machine learning, a feature may be considered as an individual measurable property or characteristic of a phenomenon (e.g. the heartbeat as represented by an ECG signal) being observed. Choosing informative, discriminating and independent features may result in effective algorithms in pattern recognition, classification and regression.

Figure 7:
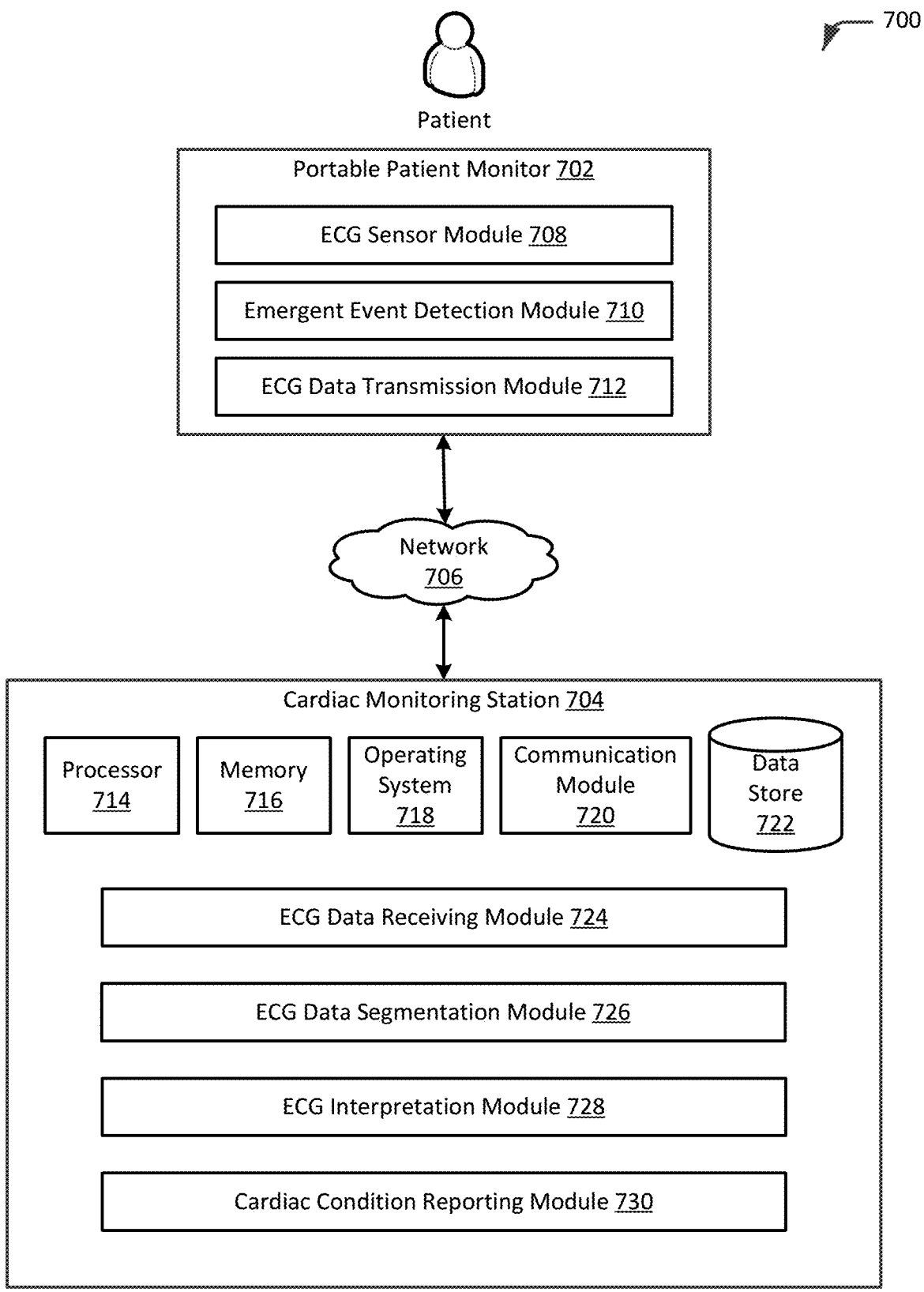
FIG. 7 is a block diagram illustrating selected components of an example remote cardiac monitoring system that processes segmented ECG signals, in accordance with an embodiment of the present disclosure.

FIG. 7 is a block diagram illustrating selected components of an example remote cardiac monitoring system 700 that utilizes machine learning to detect cardiac conditions, in accordance with an embodiment of the present disclosure. More specifically, remote cardiac monitoring system 700 illustrated in FIG. 7 can be understood as enabling a portable patient monitor 702 and a cardiac monitoring station 704 to interact with each other to provide remote monitoring of a patient for diagnosis of a cardiac condition. In such embodiments, portable patient monitor 702 and cardiac monitoring station 704 can communicate with each other via a network 706. Note that only one portable patient monitor 702 is illustrated in remote cardiac monitoring system 700 in FIG. 7 for purposes of clarity and, as such, it will be appreciated that other embodiments may include more than one portable patient monitor 702 (e.g., two, three, tens, or indeed, any suitable number of portable patient monitors).

Network 706 may be a local area network (such as a home-based or office network), a wide area network (such as the Internet), a peer-to-peer network (such as a Bluetooth connection), or a combination of such networks, whether public, private, or both. In certain embodiments, at least a portion of the functionality associated with network 706 is provided by a cellular data network, thereby making it easier for patients using portable patient monitors 702 to leverage the functionality/features of such portable devices in leveraging the services provided by cardiac monitoring station 704. In general, communications amongst the various entities and resources described herein may occur via wired or wireless connections, such as may be provided by Wi-Fi or mobile data networks.

As illustrated in FIG. 7, portable patient monitor 702 facilitates the monitoring of the cardiac rhythm of a patient's heart. To this end, in one embodiment, portable patient monitor 702 includes one or more software modules configured to implement certain of the functionalities disclosed herein, and optionally further includes hardware configured to enable such implementation. This hardware may include, but is not limited to, a processor, a memory, an operating system, a communication module, and a data store, as well as other components. In one example implementation, portable patient monitor 702 can be a relatively small device, such as a Holter monitor, a wireless ambulatory ECG, or an implantable loop recorder, which can be worn by the patient and which is configured to continuously or intermittently monitor the patient's heart activity. In one such embodiment, and as shown in FIG. 7, portable patient monitor 702 includes an ECG sensor module 708, an emergent event detection module 710, and an ECG data transmission module 712. ECG sensor module 708 is configured to acquire an ECG signal from a patient. In some embodiments, ECG sensor module 708 is also configured to digitize the acquired ECG signal. Emergent event detection module 710 is configured to process the acquired ECG signal to detect emergent events that are manifested in the ECG signal. ECG data transmission module 712 is configured to transmit or otherwise provide the acquired ECG signal to a remote monitoring system, such as cardiac monitoring station 704. In some embodiments, portable patient monitor 702 can also provide information regarding a detected emergent event or events to the remote monitoring system.

Referring still to the example embodiment illustrated in FIG. 7, cardiac monitoring station 704 can be configured to facilitate the detection of manifestations of cardiac conditions recorded during extend ECG monitoring of a patient using portable patient monitor 702, for instance. In some such embodiments, cardiac monitoring station 704 is also configured to report emergent cardiac events and/or non-emergent cardiac events detected by remote cardiac monitoring system 700. For example, the emergent cardiac events can be detected by portable patient monitor 702 and notification of detected emergent cardiac events provided to cardiac monitoring station 704 for reporting. To this end, in one embodiment, cardiac monitoring station 704 includes one or more software modules configured to implement certain of the functionalities disclosed herein, and optionally further includes hardware configured to enable such implementation. This hardware may include, but is not limited to, a processor 714, a memory 716, an operating system 718, a communication module 720, and a data store 722. In various embodiments, additional components (not illustrated, such as a display, input/output interface, user interface, etc.) or a subset of the illustrated components can be employed without deviating from the scope of the present disclosure. For instance, in various embodiments, cardiac monitoring station 704 may not include one or more of the components illustrated in FIG. 7, but cardiac monitoring station 704 may connect or otherwise couple to the one or more components via a communication interface, such as communication module 720 for example.

Processor 714, memory 716, operating system 718, communication module 720, and data store 722 of cardiac monitoring station 704 are similar to processor 202, memory 204, operating system 206, communication module 208, and data store 210 of ECG signal segmentation system 200 of FIG. 2. The previous relevant discussion with respect to components and features ECG signal segmentation system 200 of FIG. 2 that are similar in cardiac monitoring station 704 of FIG. 7 is equally applicable here, including the previous relevant discussion with respect to processor 202, memory 204, operating system 206, communication module 208, and data store 210. For instance, processor 714 may be designed to control the operations of the various other components of cardiac monitoring station 704 and, as such, may include any processing unit suitable for use in cardiac monitoring station 704.

As further shown in FIG. 7, cardiac monitoring station 704 includes an ECG data receiving module 724, an ECG data segmentation module 726, an ECG interpretation module 728, and a cardiac condition reporting module 730. ECG data receiving module 724 is configured to receive ECG signal data, such as an ECG signal transmitted or otherwise provided by a patient monitor, such as portable patient monitor 702. In some embodiments, the ECG signal data may include information regarding emergent events detected in the ECG signal. ECG data segmentation module 726 is configured to segment the received ECG signal data in accordance with various embodiments of the techniques disclosed herein. In some such embodiments, ECG data segmentation module 726 is also configured to generate an ECG data set representing the received ECG signal data using the generated ECG segments in accordance with various embodiments of the techniques disclosed herein. ECG interpretation module 728 is configured to process the received ECG signal data (e.g., the ECG data set representing the received ECG signal) to detect non-emergent events that are manifested in the ECG signal data. Note that this processing may include analysis of broad ECG signal context (e.g., the additional properties or characteristics of the heartbeats as included in the feature vectors, for instance) and/or large ECG signal buffers. Cardiac condition reporting module 730 is configured to generate ECG signal diagnostic reports. The reports may include diagnostic reports of the emergent events detected by a patient monitor such as portable patient monitor 702, for instance, and/or diagnostic reports of the non-emergent ECG signal interpretation performed by cardiac monitoring station 704.

In various embodiments, additional components or a subset of the illustrated components can be employed without deviating from the scope of the present disclosure. For instance, other embodiments may integrate the various functionalities of cardiac monitoring station 704, including ECG data receiving module 724, ECG data segmentation module 726, ECG interpretation module 728, and cardiac condition reporting module 730 into fewer modules (e.g., one, two, or three) or more modules (e.g., five or six, or more). In addition, further note that the various components of cardiac monitoring station 704 may be distributed across additional machines. In some cases, one or more of ECG data receiving module 724, ECG data segmentation module 726, ECG interpretation module 728, and cardiac condition reporting module 730 may be downloaded from a server computing system onto cardiac monitoring station 704 and/or portable patient monitor 702 for local execution. In some cases, the functionality provided by one or more of ECG data receiving module 724, ECG data segmentation module 726, ECG interpretation module 728, and cardiac condition reporting module 730 may be provided on a server computing system communicatively coupled to cardiac monitoring station 704. In a more general sense, the degree of integration and distribution of the functional component(s) provided herein can vary greatly from one embodiment to the next, as will be appreciated in light of this disclosure.

Figure 8:
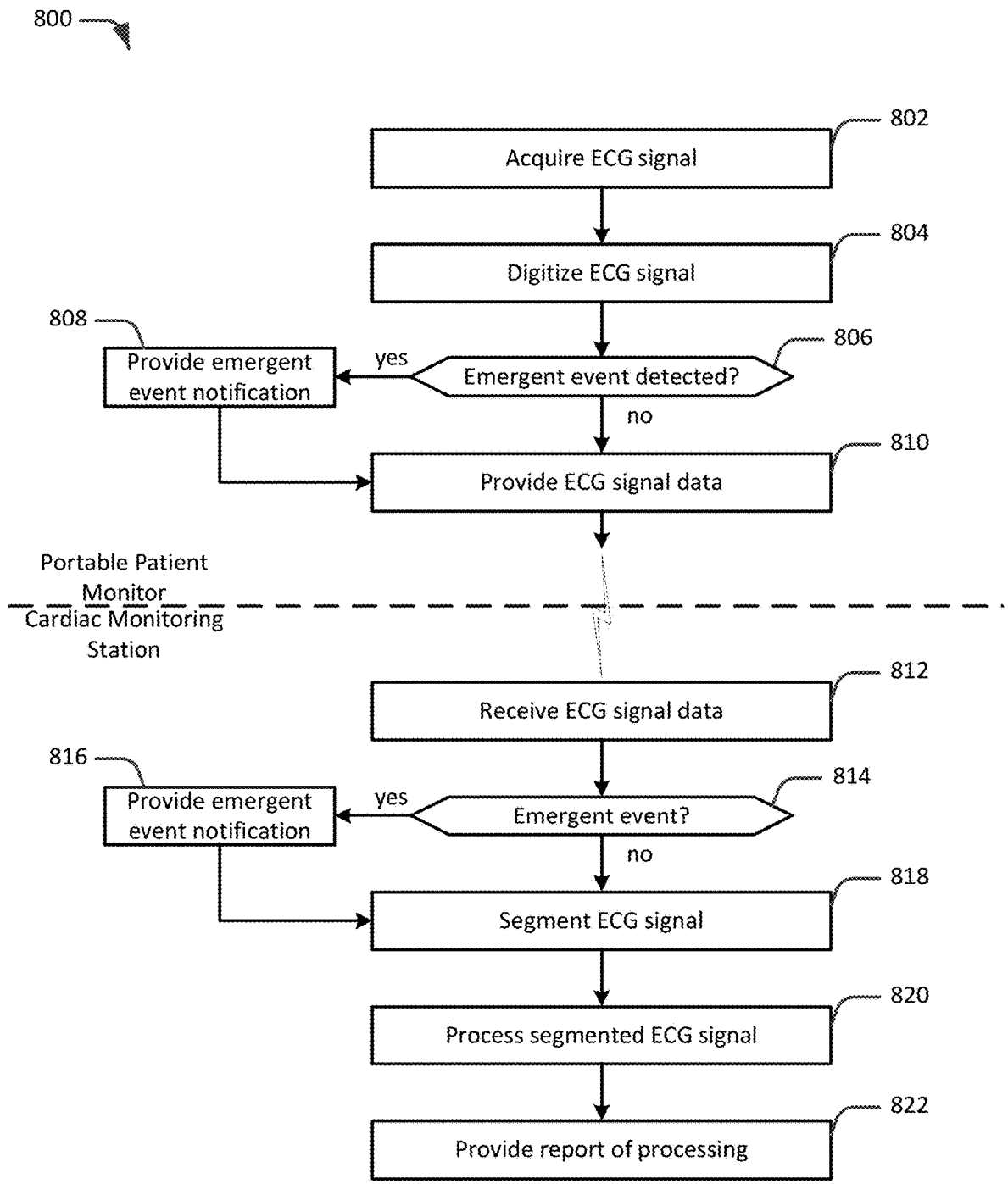
FIG. 8 is a flow diagram illustrating an example process for remote ECG monitoring of a patient using segmented ECG signals, in accordance with an embodiment of the present disclosure.

FIG. 8 is a flow diagram illustrating an example process 800 for remote ECG monitoring of a patient, in accordance with an embodiment of the present disclosure. As shown in FIG. 8, operations 802-810 of process 800 may be performed by a portable patient monitor, such as portable patient monitor 702, and operations 812-822 may be performed by a cardiac monitoring station, such as cardiac monitoring station 704. In particular, and according to one embodiment, operations 802-810 may be performed by a portable patient monitor that is monitoring a patient's heart activity, and operations 812-822 may be performed by a cardiac monitoring station that is processing ECG signal data that is representative of the patient's heart activity as monitored by the portable patient monitor for existence (or non-existence) of a cardiac condition. In some such embodiments, the cardiac monitoring station can be operating remotely from the portable patient monitor. The operations, functions, or actions described in the respective blocks of example process 800 may be stored as computer-executable instructions in a computer-readable medium, such as memory 716 and/or data store 722 of cardiac monitoring station 704 and/or suitable memory of portable patient monitor 702.

As will be further appreciated in light of this disclosure, for this and other processes and methods disclosed herein, the functions performed in the processes and methods may be implemented in differing order. Additionally or alternatively, two or more operations may be performed at the same time or otherwise in an overlapping contemporaneous fashion. Furthermore, the outlined actions and operations are only provided as examples, and some of the actions and operations may be optional, combined into fewer actions and operations, or expanded into additional actions and operations without detracting from the essence of the disclosed embodiments. To this end, each of the example processes depicted is provided to give one example embodiment and is not intended to limit the process to any particular physical or structural configuration.

With reference to example process 800 of FIG. 8, at operation 802, the portable patient monitor acquires an ECG signal from a patient. At operation 804, the portable patient monitor digitizes the acquired ECG signal. At operation 806, the portable patient monitor process the ECG signal for emergent events. If an emergent event is detected, then, at operation 808, the portable patient monitor provides a notification of the detected emergent event. At operation 810, the portable patient monitor transmits or otherwise provides the ECG signal data to the cardiac monitoring station. In some embodiments, the ECG signal data includes information regarding detected emergent events. The portable patent monitor can continue monitoring the patient.

At operation 812, the cardiac monitoring station receives the ECG signal data provided by the portable patient monitor. At operation 814, the cardiac monitoring station checks to determine whether information regarding detected emergent events is included in or with the received ECG signal data. If information regarding detected emergent events is included in or with the received ECG signal data, then, at operation 816, the cardiac monitoring station provides a notification of the detected emergent events (e.g., the emergent events reported by the portable patient monitor). At operation 818, the cardiac monitoring station segments the received ECG signal. In some embodiments, the cardiac monitoring station generates an ECG data set that represents the received ECG signal using the ECG segments generated from segmenting the received ECG signal. The cardiac monitoring station can perform the ECG signal segmentation and/or the ECG data set generation in accordance with various embodiments of the techniques disclosed herein. At operation 820, the cardiac monitoring station processes the segmented ECG signal (e.g., the ECG data set representing the received ECG signal data), For example, the segmented ECG signal can be processed to detect non-emergent events. At operation 822, the cardiac monitoring station provides a report of the results of the processing. For example, the report may include information regarding detected emergent events and/or information regarding detected non-emergent events.

In accordance with an embodiment, techniques are disclosed for remote ECG monitoring using machine learning. According to an embodiment, a remote cardiac monitoring system includes a portable patient monitor and a cardiac monitoring station, which includes a trained ECG interpretation module for predicting the existence of cardiac conditions in ECG monitoring data. In brief, the portable patent monitor is operable to acquire and record ECG signals from a patient and transmit the ECG data to the cardiac monitoring station. The cardiac monitoring station receives the ECG data and, utilizing the trained ECG interpretation module, makes a prediction (e.g., inference) as to the existence (or non-existence) of a cardiac condition as manifested by the input ECG data.

In a training data preparation phase, ECG data is first obtained from which to generate training data to train an ECG interpretation module. The ECG data may include ECG signals obtained from a large number of people including patients experiencing a cardiac condition and/or not experiencing a cardiac condition. The obtained ECG signals can then be processed (e.g. segmented as described herein) to identify patterns in the ECG data, and the identified patterns of ECG data labeled as either being indicative of a cardiac condition or not indicative of a cardiac condition. In some such embodiments, the patterns of ECG data may be labeled to indicate a particular cardiac condition, such as atrial fibrillation, to provide one example.

In embodiments fixed size ECG segments surrounding the marked heartbeats can be highlighted. In cases in which some segments are not overlapping, it cannot be assured that all of the ECG signal fragments are contained in the data (i.e. an ECG fragment may not be contained in the data). The resolution to this problem is the construction of the machine learning data table and an introduction of an artificial beat (x) to include the not included ECG fragment between appropriate segments in accordance with the techniques described herein.

In some such embodiments, additional information, such as heart rate information and other features regarding a heartbeat, for instance, can be added as part of or otherwise associated with the labeled ECG data segments. Such additional information can be specified using feature vectors, where each vector includes features specific for the given heartbeat. By way of an example, and in one example implementation, each feature vector may contain information describing P-wave information, T-wave information including onset location, offset location, duration, shape/morphology, amplitude, other waves information including Q, R and S characteristics, morphologies, durations and amplitudes, noise level information surrounding the given beat and acceleration information measured through the built-in accelerometer built in to the patient portable monitor, and other information containing beat information collected from non-ECG sensors, including PPG signal, blood pressure signal, and blood oxygen saturation information, to provide some examples.

As used in the present disclosure, the terms "engine" or "module" or "component" may refer to specific hardware implementations configured to perform the actions of the engine or module or component and/or software objects or software routines that may be stored on and/or executed by general purpose hardware (e.g., computer-readable media, processing devices, etc.) of the computing system. In some embodiments, the different components, modules, engines, and services described in the present disclosure may be implemented as objects or processes that execute on the computing system (e.g., as separate threads). While some of the system and methods described in the present disclosure are generally described as being implemented in software (stored on and/or executed by general purpose hardware), specific hardware implementations, firmware implements, or any combination thereof are also possible and contemplated. In this description, a "computing entity" may be any computing system as previously described in the present disclosure, or any module or combination of modulates executing on a computing system.

Terms used in the present disclosure and in the appended claims (e.g., bodies of the appended claims) are generally intended as "open" terms (e.g., the term "including" should be interpreted as "including, but not limited to," the term "having" should be interpreted as "having at least," the term "includes" should be interpreted as "includes, but is not limited to," etc.).

Additionally, if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to embodiments containing only one such recitation, even when the same claim includes the introductory phrases "one or more" or "at least one" and indefinite articles such as "a" or "an" (e.g., "a" and/or "an" should be interpreted to mean "at least one" or "one or more"); the same holds true for the use of definite articles used to introduce claim recitations.

In addition, even if a specific number of an introduced claim recitation is explicitly recited, such recitation should be interpreted to mean at least the recited number (e.g., the bare recitation of "two widgets," without other modifiers, means at least two widgets, or two or more widgets). Furthermore, in those instances where a convention analogous to "at least one of A, B, and C, etc." or "one or more of A, B, and C, etc." is used, in general such a construction is intended to include A alone, B alone, C alone, A and B together, A and C together, B and C together, or A, B, and C together, etc.

All examples and conditional language recited in the present disclosure are intended for pedagogical examples to aid the reader in understanding the present disclosure, and are to be construed as being without limitation to such specifically recited examples and conditions. Although example embodiments of the present disclosure have been described in detail, various changes, substitutions, and alterations could be made hereto without departing from the spirit and scope of the present disclosure. Accordingly, it is intended that the scope of the present disclosure be limited not by this detailed description, but rather by the claims appended hereto.

The invention claimed is:
1. A method to segment an electrocardiogram (ECG) signal, the method comprising:
   detecting, by one or more processors, a plurality of consecutive heartbeats in an ECG signal;

segmenting, by the one or more processors, the ECG signal into a plurality of ECG segments surrounding the detected plurality of consecutive heartbeats;

generating, by the one or more processors, an ECG data set by joining consecutive ECG segments, wherein the ECG data set represents the detected plurality of consecutive heartbeats;

detecting, by the one or more processors, one or more adjacent pairs of ECG segments within the ECG data set that do not overlap in time;

for each of the pairs of non-overlapping ECG segments, including an artificial heartbeat within the ECG data set to indicate a missing ECG fragment between the pair of non-overlapping ECG segments, wherein the artificial heartbeat is a marker between the pair of non-overlapping ECG segments;

generating, by the one or more processors, a machine learning input data table using the ECG data set representing the detected plurality of consecutive heartbeats and including the artificial heartbeats, such that the machine learning data table includes a continuous representation of ECG data;

detecting one or more emergent events or information regarding detected non-emergent events based on the machine learning input data table; and generating a report based on the detections, wherein the report includes information regarding the detected one or more emergent events or information regarding detected non-emergent events.

2. The method of claim 1, wherein segmenting the ECG signal into the plurality of ECG segments comprises segmenting the ECG signal into fixed-size ECG segments.

3. The method of claim 1, wherein each ECG segment of the plurality of ECG segments is of a duration to include a QRS complex, a P wave, and a T wave.

4. The method of claim 1, wherein the ECG data set includes instantaneous heart rate values or R-R interval values representative of distances between consecutive pairs of heartbeats.

5. The method of claim 1, wherein the ECG data set includes one or more feature vectors, wherein a feature vector includes features specific for a corresponding heartbeat, a feature specifying the heartbeat's morphology, ECG signal condition, or physiological information gathered through non-ECG sensors, correlated with the heartbeat data.

6. The method of claim 5, further comprising two feature vectors specific to the corresponding heartbeat, wherein a first feature vector includes heart rate information and a second feature vector includes other properties or characteristics.

7. The method of claim 1, wherein the artificial heartbeat is a marker (x) to indicate the artificial heartbeat.

8. The method of claim 1, wherein the ECG segments are indicated with a black dot to indicate a heartbeat.

9. A system to segment an electrocardiogram (ECG) signal, the system comprising:

one or more non-transitory machine-readable mediums configured to store instructions; and one or more processors configured to execute the instructions stored on the one or more non-transitory machine-readable mediums, wherein execution of the instructions causes the one or more processors to:

detect, by the one or more processors, N consecutive heartbeats in an ECG signal;

segment, by the one or more processors, the ECG signal into a plurality of ECG segments surrounding the detected N consecutive heartbeats;

generate, by the one or more processors, an ECG data set by joining consecutive ECG segments, wherein the ECG data set represents the detected N consecutive heartbeats;

detect, by the one or more processors, one or more adjacent pairs of ECG segments within the ECG data set that do not overlap in time;

for each of the pairs of non-overlapping ECG segments, including an artificial heartbeat within the ECG data set to indicate a missing ECG fragment between the pair of non-overlapping ECG segments, wherein the artificial heartbeat is a marker between the pair of non-overlapping ECG segments;

generate, by the one or more processors, a machine learning input data table using the ECG data set representing the detected N consecutive heartbeats and including the artificial heartbeats, such that the machine learning input data table includes a continuous representation of ECG data;

detect one or more emergent events or information regarding detected non-emergent events based on the machine learning input data table; and generate a report based on the detections, wherein the report includes information regarding the detected one or more emergent events or information regarding detected non-emergent events.

10. The system of claim 9, wherein the plurality of ECG segments includes fixed-size ECG segments.

11. The system of claim 9, wherein each ECG segment of the plurality of ECG segments is of a duration to include a QRS complex, a P wave, and a T wave.

12. The system of claim 9, wherein the ECG data set includes instantaneous heart rate values or R-R interval values representative of distances between consecutive pairs of heartbeats.

13. The system of claim 9, wherein the ECG data set includes one or more feature vectors, wherein a feature vector includes features specific for a corresponding heartbeat.

14. The system of claim 13, further comprising two feature vectors specific to the corresponding heartbeat, wherein a first feature vector includes heart rate information and a second feature vector includes other properties or characteristics.

15. The system of claim 9, wherein the ECG data set includes one or more feature vectors, wherein a feature vector includes a feature specifying the heartbeat's morphology.

16. The system of claim 9, wherein the ECG data set includes one or more feature vectors, wherein a feature vector includes an ECG signal condition.

17. The system of claim 9, wherein the ECG data set includes one or more feature vectors, wherein a feature vector includes physiological information correlated with a corresponding heartbeat.

18. The system of claim 9, wherein the artificial heartbeat is a marker (x) to indicate the artificial heartbeat.

19. The system of claim 9, wherein the ECG segments are indicated with a black dot to indicate a heartbeat.

* * * * *